United States Patent
Dominguez et al.

(10) Patent No.: US 9,248,384 B2
(45) Date of Patent: Feb. 2, 2016

(54) FAT PROCESSING SYSTEM

(71) Applicant: Allergan, Inc., Irvine, CA (US)

(72) Inventors: Zachary Dominguez, Santa Barbara, CA (US); Justin Schwab, Santa Barbara, CA (US); Tiago Bertolote, Geneva (CH); Jason Metzner, Carpinteria, CA (US); Ethan Franklin, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 56 days.

(21) Appl. No.: 14/044,594

(22) Filed: Oct. 2, 2013

(65) Prior Publication Data

US 2015/0093362 A1   Apr. 2, 2015

(51) Int. Cl.
| | |
|---|---|
| *B01D 17/00* | (2006.01) |
| *B01D 33/00* | (2006.01) |
| *B01D 33/01* | (2006.01) |
| *A61L 27/36* | (2006.01) |
| *A61M 1/00* | (2006.01) |

(52) U.S. Cl.
CPC ............... *B01D 17/08* (2013.01); *B01D 17/10* (2013.01); *B01D 33/00* (2013.01); *B01D 33/01* (2013.01); *A61L 27/3604* (2013.01); *A61L 27/3683* (2013.01); *A61M 1/0005* (2013.01); *B01D 2221/10* (2013.01)

(58) Field of Classification Search
CPC .. B01D 33/01; B01D 33/015; B01D 33/0158; B01D 33/0183; C12M 33/14
See application file for complete search history.

(56) References Cited

U.S. PATENT DOCUMENTS

| | | | |
|---|---|---|---|
| 4,605,691 A | | 8/1986 | Balazs et al. |
| 4,627,444 A | * | 12/1986 | Brooker ..................... 600/571 |
| 4,909,932 A | * | 3/1990 | Monnet ......................... 210/98 |
| 5,650,317 A | | 7/1997 | Chang et al. |
| 5,716,404 A | | 2/1998 | Vacanti |
| 5,814,511 A | | 9/1998 | Chang et al. |
| 5,972,385 A | | 10/1999 | Liu et al. |
| 6,082,364 A | | 7/2000 | Balian et al. |
| 6,083,912 A | | 7/2000 | Khouri |
| 6,129,761 A | | 10/2000 | Hubbell et al. |
| 6,171,610 B1 | | 1/2001 | Vacanti et al. |
| 6,214,045 B1 | | 4/2001 | Corbitt |
| 6,239,105 B1 | | 5/2001 | Brewitt et al. |
| 6,582,960 B1 | | 6/2003 | Martin et al. |
| 6,638,308 B2 | | 10/2003 | Corbitt |
| 6,656,488 B2 | | 12/2003 | Yi et al. |
| 6,666,893 B2 | | 12/2003 | Burg et al. |
| 6,777,231 B1 | | 8/2004 | Katz et al. |
| 6,881,226 B2 | | 4/2005 | Corbitt |
| 6,916,603 B2 | | 7/2005 | Baron et al. |
| 6,991,652 B2 | | 1/2006 | Burg et al. |
| 7,015,037 B1 | | 3/2006 | Furcht et al. |
| 7,129,209 B2 | | 10/2006 | Rhee et al. |
| 7,285,266 B2 | | 10/2007 | Vournakis et al. |
| 7,316,822 B2 | | 1/2008 | Binette et al. |
| 7,390,484 B2 | | 6/2008 | Fraser et al. |
| 7,445,793 B2 | | 11/2008 | Niwa et al. |
| 7,501,115 B2 | | 3/2009 | Fraser et al. |
| 7,514,075 B2 | | 4/2009 | Hedrick et al. |
| 7,560,276 B2 | | 7/2009 | Harmon et al. |
| 7,651,684 B2 | | 1/2010 | Hedrick et al. |
| 7,767,452 B2 | | 8/2010 | Kleinsek et al. |
| 7,799,767 B2 | | 9/2010 | Lamberti et al. |
| 7,875,296 B2 | | 1/2011 | Binette et al. |
| 8,053,423 B2 | | 11/2011 | Lamberti et al. |
| 8,066,691 B2 | | 11/2011 | Khouri |
| 8,137,705 B2 | | 3/2012 | Doyle et al. |
| 8,153,591 B2 | | 4/2012 | Masters et al. |
| 2004/0092011 A1 | | 5/2004 | Wilkison et al. |
| 2007/0251531 A1 | | 11/2007 | Khouri |
| 2008/0243028 A1 | * | 10/2008 | Howard et al. ............... 600/565 |
| 2008/0317718 A1 | | 12/2008 | Yoshimura |
| 2009/0098177 A1 | | 4/2009 | Werkmeister et al. |
| 2009/0123547 A1 | | 5/2009 | Hill |
| 2009/0124552 A1 | | 5/2009 | Hill |
| 2009/0162415 A1 | | 6/2009 | Huang et al. |
| 2009/0312746 A1 | | 12/2009 | Khouri |
| 2010/0010627 A1 | | 1/2010 | Matheny |
| 2011/0070281 A1 | | 3/2011 | Altman et al. |
| 2011/0150823 A1 | | 6/2011 | Huang |
| 2011/0213336 A1 | | 9/2011 | Cucin |
| 2012/0010146 A1 | | 1/2012 | Han et al. |
| 2012/0076868 A1 | | 3/2012 | Lamberti et al. |
| 2012/0156265 A1 | | 6/2012 | Binette et al. |
| 2012/0209248 A1 | | 8/2012 | Gurtner et al. |

FOREIGN PATENT DOCUMENTS

| | | |
|---|---|---|
| EP | 1476202 B1 | 1/2009 |
| WO | 2007124478 A2 | 11/2007 |
| WO | 2008063569 A1 | 5/2008 |
| WO | 2008148026 A1 | 12/2008 |
| WO | 2008148071 A2 | 12/2008 |
| WO | 2009003135 A1 | 12/2008 |
| WO | 2009047346 A1 | 4/2009 |

(Continued)

*Primary Examiner* — Renee Claytor
*Assistant Examiner* — Susan E Fernandez
(74) *Attorney, Agent, or Firm* — Linda Allyson Nassif

(57) ABSTRACT

Methods and devices for treating lipoaspirate for use in fat grafting procedures are provided and generally include a canister for containing lipoaspirate, a separation mechanism structured to separate both oils and other materials from cellular components of lipoaspirate contained in the canister. The separation mechanism includes filters having different filtering capacities, for example, different pore sizes.

5 Claims, 6 Drawing Sheets

(56) References Cited

FOREIGN PATENT DOCUMENTS

| WO | 2009085548 | A2 | 7/2009 |
| WO | 2009103818 | A1 | 8/2009 |
| WO | 2009115581 | A2 | 9/2009 |
| WO | 2009155583 | A1 | 12/2009 |
| WO | 2010026299 | A1 | 3/2010 |
| WO | 2010127310 | A1 | 11/2010 |
| WO | 2011072399 | A1 | 6/2011 |
| WO | 2012006587 | A2 | 1/2012 |
| WO | WO 2012019103 | A2 * | 2/2012 |

* cited by examiner

FAT PROCESSING SYSTEM

BACKGROUND

The present invention generally relates to fat grafting and more specifically relates to a system for processing fat prior to reintroduction into the body.

Autologous fat transfer (AFT), also known as fat grafting, is a process by which fat is harvested from one part of a human body and injected into another part of the same person's body where additional bulk may be needed or desired for cosmetic and/or aesthetic purposes. Clinical applications for autologous fat transfer are expanding rapidly with recent reported use in breast reconstruction and augmentation, buttock enhancement, treatment of congenital tissue defects, facial reconstruction, and skin rejuvenation. Although this is a very attractive approach and there is an increased trend in replacement of soft tissue volume with AFT, typical survival rates of grafted fat may be poor and overall results may not be satisfactory.

WO 2008/148071 discloses kits, tools, and methods are described for harvesting, processing, and using injectable dermis in volume filling procedures.

WO 2009/003135 discloses system for harvesting fat through liposuction, concentrating the aspirate so obtained, and then re-injecting the concentrated fat into a patient.

There still remains a need for improved systems and methods for processing harvested fat for later use in fat grafting procedures.

SUMMARY

The present invention generally comprises a device or system that is structured to be useful for separating unwanted fluids/materials from a sample of lipoaspirate. The resulting cellular material is subsequently used for reintroducing into the body for augmentation or tissue replacement.

During fat grafting procedures, adipose tissue is removed from the body, for example, using an aspirating device, and reintroduced into another part of the body, for example, by means of a syringe. The lipoaspirate initially includes several types of material, for example, undamaged and damaged fat cells, oils, blood cells, intracellular fluids and other materials, some of which may are not ideally suited for reintroduction into the body, for example, for reasons such as safety and graft efficacy.

In general, the three main types of material that comprises the lipoaspirate are viable fat cells, blood/tumescent fluid, and oil (ruptured and/or nonviable fat cells). The present devices and systems are effective to separate at least two or three of these components to achieve a product comprising primarily undamaged adipose and stem cells.

Accordingly a device is provided for treating or processing lipoaspirate for use in fat grafting procedures.

The device comprises, for example, a container or canister for receiving and/or storing the lipoaspirate after removal from a patient. Lipoaspirate is delivered to the canister by means of an inlet orifice or valve, for example, connected to a source of negative pressure, or vacuum. Alternatively, lipoaspirate may be delivered to the canister without using suction, for example, by pouring the lipoaspirate into the canister through a top opening, for example. The canister may also include an outlet orifice or valve for facilitating removal of the desired, processed material, for example, a material primarily comprising viable fat cells.

The device further includes a separation mechanism structured to separate both oils and other materials from cellular components of lipoaspirate contained in the canister. The separation mechanism comprises, for example, one or more filter elements, for example, a sieve or filter screen for separating viable fat cells from damaged cells, oils, and other liquids. For example, the filter screen, or sieve, may comprise any number of known materials that are capable of sorting or dividing components by size. For example, the filter element may comprise a filter paper having a suitable pore size, a mesh with varying pitch, or other material known in the art capable of separating lipoaspirate components.

The device further comprises an activation mechanism structured to activate the separation mechanism. For example, the activation mechanism is structured to move at least one of the first and the second filter elements within the canister. The activation mechanism may comprise one or more plunger mechanisms, slidably contained in the canister and coupled to the filter elements. The one or more plungers may be operable by means of a piston, for example, and function to move the one or more filter elements within the canister. The plungers may be manually operable.

BRIEF DESCRIPTION OF THE DRAWINGS

The present invention may be more clearly understood and the advantages thereof better appreciated by considering the below Detailed Description and accompanying Drawings of which.

DETAILED DESCRIPTION

Figure 1:
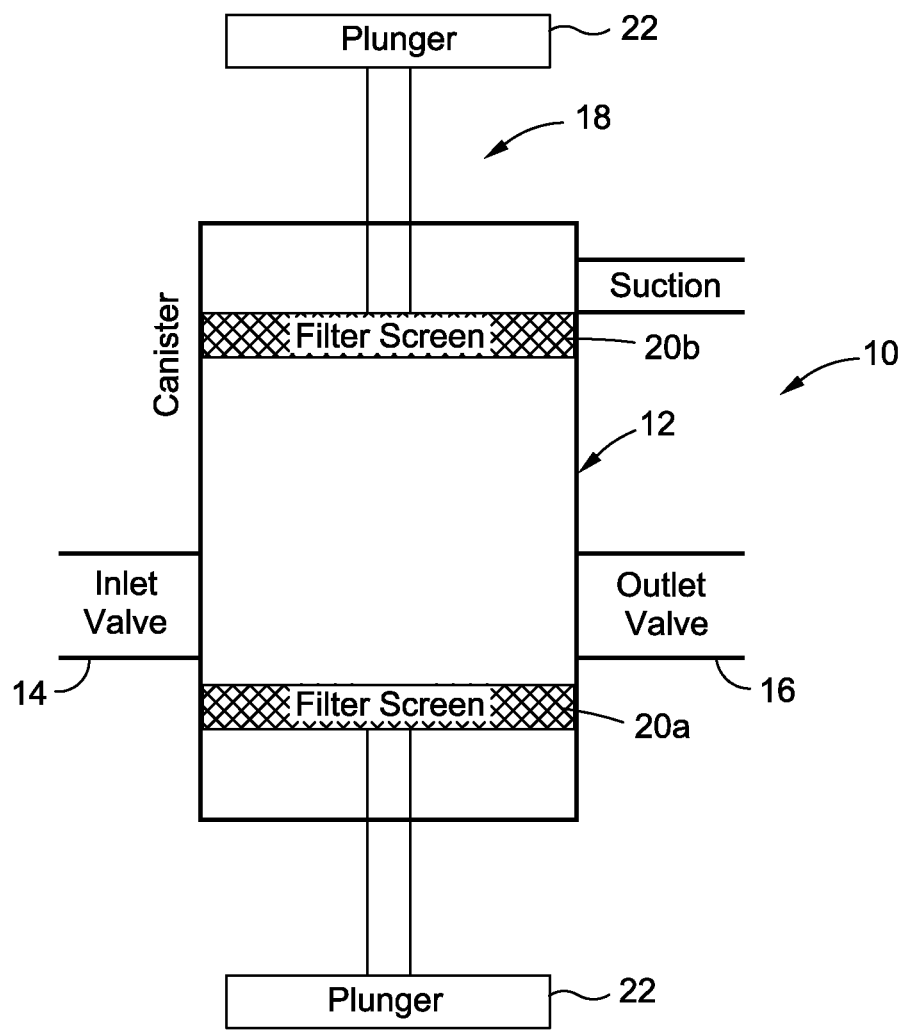
FIG. 1 is a simplified diagrammatical view of a device, in accordance with the invention, having two independently movable filter screens for separating components of lipoaspirate.

Turning now to FIG. 1, an exemplary device 10 in accordance with an embodiment of the invention is shown. The device 10 generally includes a canister 12 for containing lipoaspirate, an inlet 14, and outlet valve 16 and a separating mechanism 18 including first and second filter screens 20a, 20b and plungers 22 which are movable, for example, by manual means, in the canister 12.

The operation of the device 10 is shown in FIG. 2A-2D.

Figure 2A:
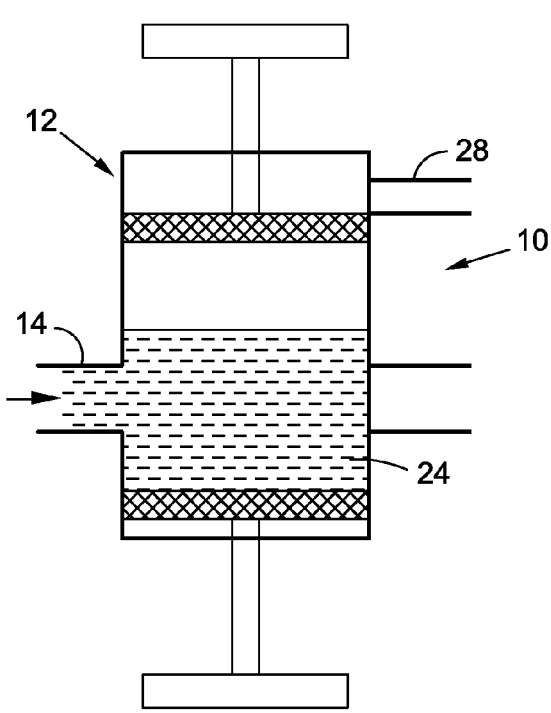
FIGS. 2A-2D show operation of the device shown in FIG. 1.
Figure 2B:
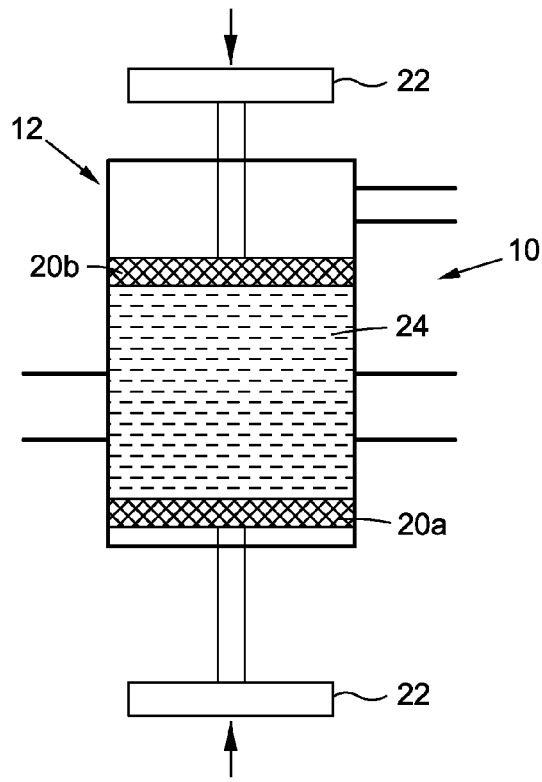

Lipoaspirate 24 is brought into canister 12, for example, drawn into the canister 12 by vacuum mechanism 28 through inlet 14 (FIG. 2A). The plungers 22 may be manually driven by a physician/operator applying force to plungers 22 as illustrated by arrows (FIG. 2B). Driving of plungers 22 forces lipoaspirate materials which can pass through the filter screens 20a, 20b into spaces in canister 12 opposing the screens 20a, 20b, thus separating the materials making up the lipoaspirate 24.

The filter screens may comprise any number of suitable materials capable of separating components of the lipoaspirate.

Advantageously, the present device 10 allows separation of lipoaspirate to a desired degree. For example, it may be desirable in certain circumstances, as determined by the physician/ operator, to remove a portion of the liquids, for example, oils, from the viable cells, leaving a minor amount or desired percentage of oil in the lipoaspirate for promoting fat graft viability. The simplicity of device 10 allows the physician/operator to control the degree or amount of separation. To further facilitate this feature, the canister 12 may be structured or made of a material, for example, a transparent polymer, that allows the physician/operator to view the content of the canister 12.

Figure 2C:
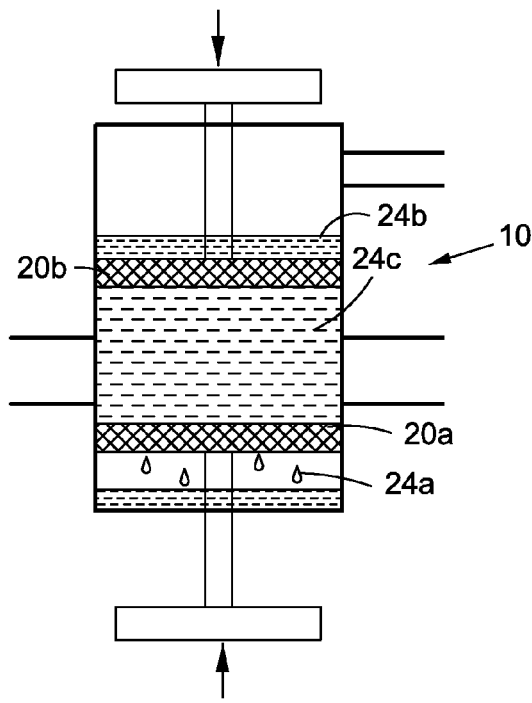
Figure 2D:
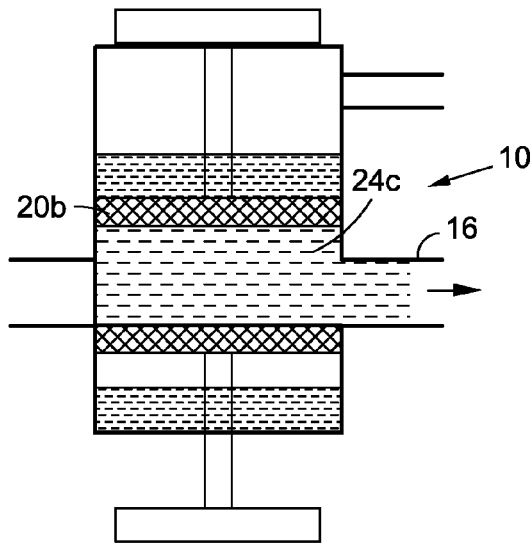

As the filter screens 20a, 20b are driven through the lipoaspirate, the lipoaspirate is separated into various components. For example, blood/tumescent fluid 24a are forced through first filter 20a, while oil 24b is forced through the second filter 20b. (FIG. 2C). After sufficient separation is achieved, viable fat cells 24c and any remaining blood/tumescent fluid and/or oils, can be removed via the outlet valve 16 (FIG. 2D).

Figure 3:
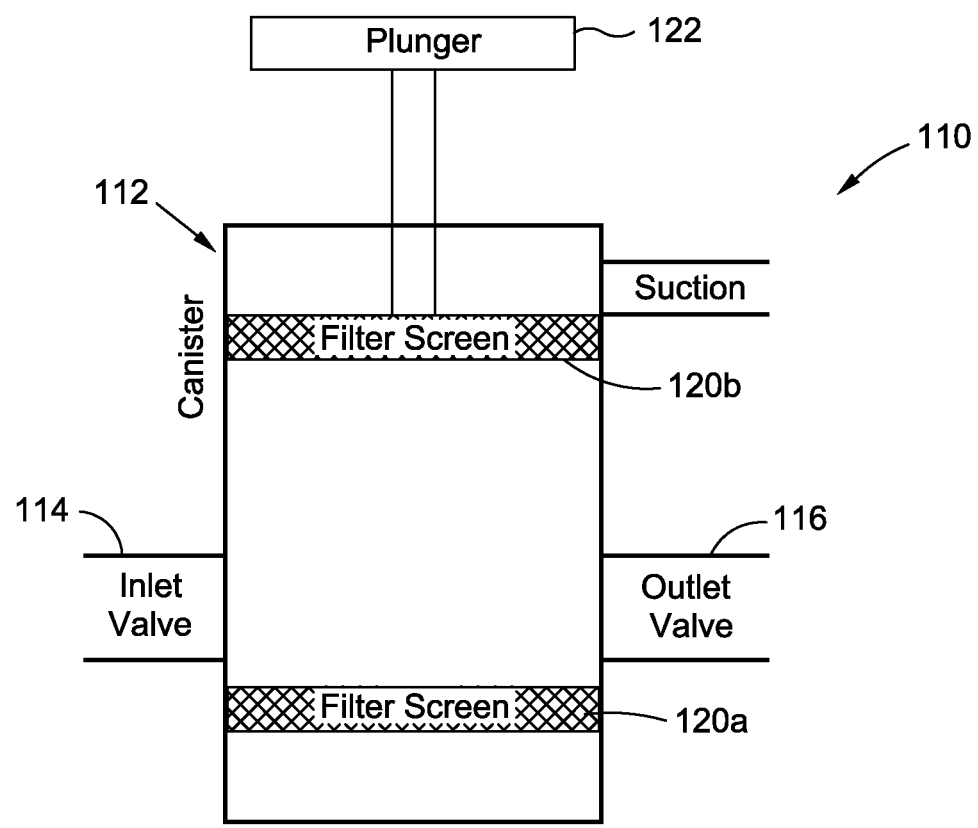
FIG. 3 shows an alternative device, in accordance with the invention, including a fixed filter screen.

FIG. 3 shows a device 110 in accordance with another embodiment of the invention. For the sake of simplicity, elements of device 110 which are similar or identical to elements of device 10 are indicated by the same reference number increased by 100.

Device 110 is similar to device 10, with a major distinction being that device 110 includes a single plunger 122 rather than multiple plungers, and a fixed filter screen 120a. Device 110 includes first and second screens 120a, 120b for separating blood/fluid and oils from fat cells. In this embodiment, the first filter screen 120a is fixed within the canister 112, while second filter screen 120b is movable in canister 112 by means of plunger 122. Outlet 116 may be positioned on an upstream side of fixed filter 120a, as shown. The physician/operator causes separation of lipoaspirate within the canister 112 by pressing on the plunger 122. Movement of second filter screen 120b into the lipoaspirate causes separation of the lipoaspirate as described elsewhere herein, leaving viable fat cells between the first and second filter screens 120a, 120b, which can be removed from canister via outlet 116.

Figure 4:
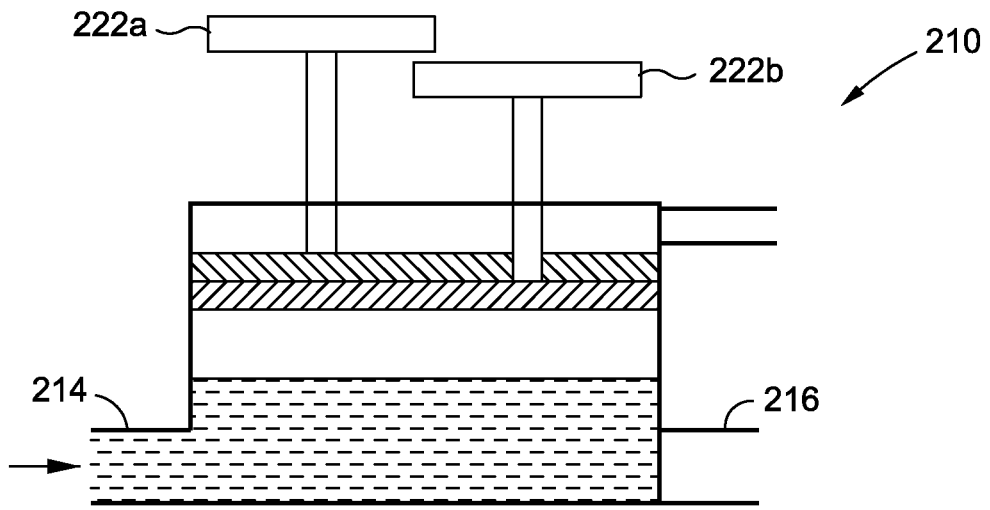
FIG. 4 shows yet another device in accordance with the invention.

FIG. 4 shows yet another device 210 in accordance with the invention. For the sake of simplicity, elements of device 210 which are similar or identical to elements of device 10 are indicated by the same reference number increased by 200.

Device 210 includes inlet 214 and outlet 216 both located on a common side of first and second filter screens 220a, 220b, for example, at a bottom side of the canister 212. This arrangement may eliminate the sensitivity associated with placing the inlet and outlet valves on the canister in a specific location (which may be dependent on how much and the type of lipoaspirate that is sampled. This arrangement ensures that all incoming fluid is below both filter screens 220a, 220b, and allows for effective drainage of tumescent fluid, which has a relatively high density, followed by complete removal of viable fat.

Figure 4A:
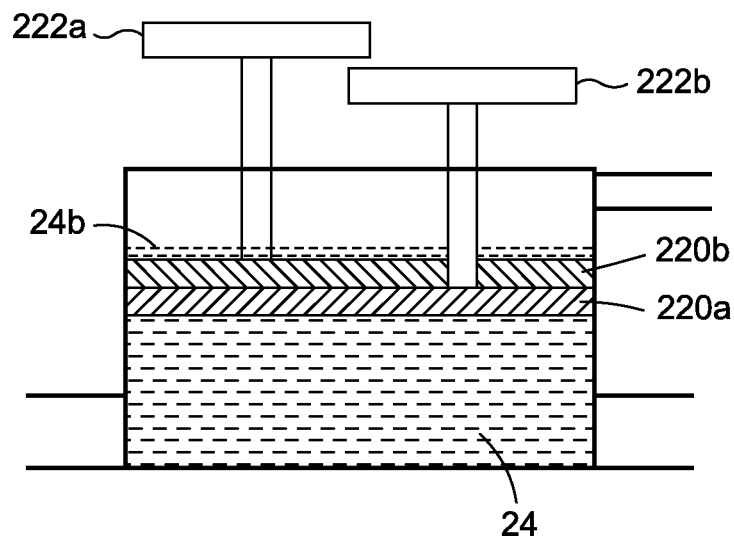
FIGS. 4A-4C show operation of the device shown in FIG. 4.
Figure 4B:
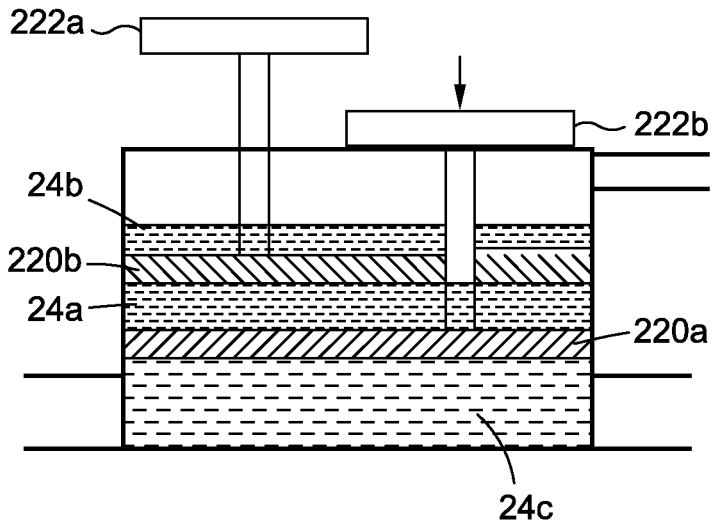
Figure 4C:
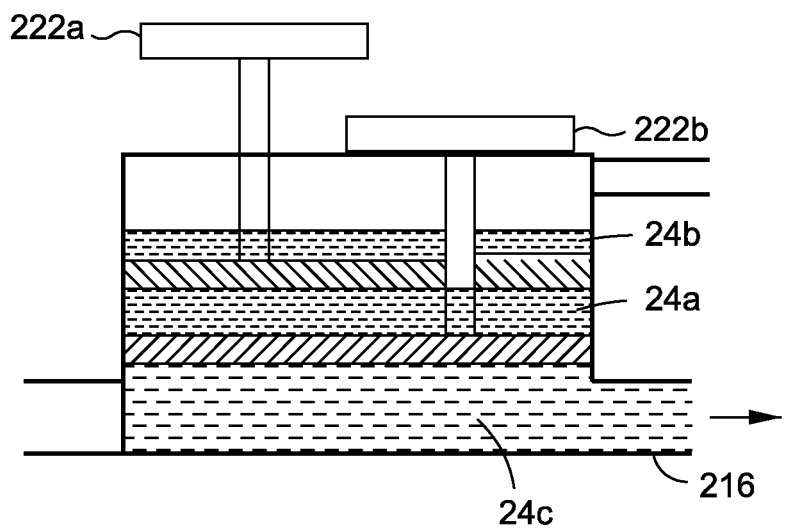

Exemplary operation of device 210 is illustrated in FIGS. 4A-4C. First and second filter screens 220a, 220b, are oriented such that first screen 220a and second screen 220b are initially directly adjacent one another (FIG. 4). Due to arrangement of plunger heads, one overlapping the other, pressure on first plunger 222a (shown as left plunger in the Figures) moves both first and second screens 220a, 220b into lipoaspirate 24 and causes separation of the oil 22b therefrom (FIG. 4A). Second plunger 222b is then pressed, independently of first plunger 222a, which moves only first filter screen 220a and filters out the blood and tumescent fluid 24a (FIG. 4B). The viable fat cells 24c are then removed through the outlet valve 216 (FIG. 4C).

Figure 5:
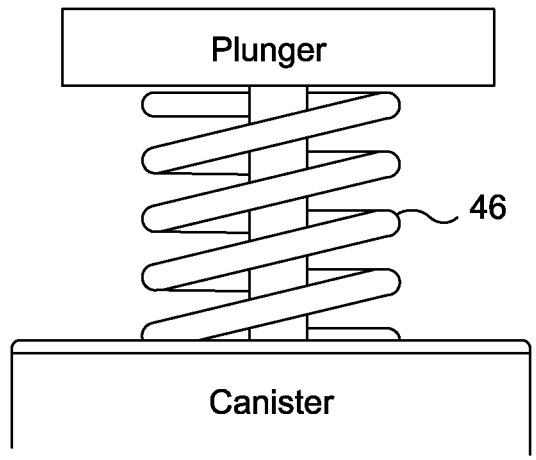
FIGS. 5 and 6 show mechanically limiting features for controlling rate of filtering.
Figure 6:
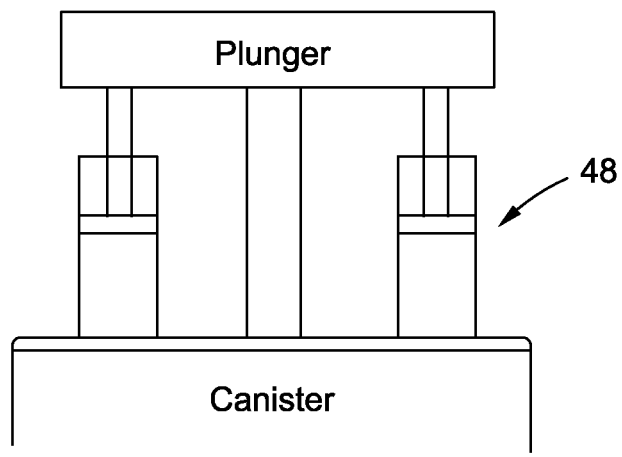

Turning now to FIG. 5, any of the aforementioned embodiments may further comprise a mechanically limiting feature for controlling filtering rate. The amount of stress applied to lipoaspirate may affect the viability of the lipoaspirate cells. Thus, in some embodiments, a mechanism is provided to control the acceleration of the plunger through the lipoaspirate and/or reduce the speed at which the filter screens are forced through the lipoaspirate. For example, the mechanically limiting feature comprise, for example, any suitable mechanism, for example, spring 46, or the like, coupled to plunger 22, 122, 222a and/or 222b. The spring 46 controls the movement of the plunger, for example, by providing a dampening effect, thereby allowing a slower and/or more consistent motion of the filter screen through the lipoaspirate, thereby reducing damage to cells. Alternatively, the mechanically limiting feature may comprise a hydraulic mechanism 48 for controlling plunger rate, such as shown in FIG. 6.

In another aspect of the invention, a method for treating lipoaspirate for use in fat grafting procedures is provided wherein the method comprises containing lipoaspirate in a container, the container including a first filter element and a second filter element, and moving the first filter element relative to a second filter element within the container to separate cellular components of the lipoaspirate from non-cellular components of the lipoaspirate. As mentioned elsewhere herein, the first filtering element may have a pore size different from a pore size of the second filtering element. Further, in some embodiments the first filtering element is capable of separating blood/tumescent fluids from cellular materials in lipoaspirate, and the second filtering element is capable of separating oils from cellular materials in lipoaspirate. In some embodiments, the container allows for viewing of the lipoaspirate during the separation, and the method may involve the step of observing the separation and stopping the moving when a desired degree of separation is achieved.

While this invention has been described with respect to various specific examples and embodiments, it is to be understood that the invention is not limited thereto and that it can be variously practiced within the scope of the invention.

What is claimed is:

1. A method for treating lipoaspirate for use in fat grafting procedures, the method comprising:
    containing lipoaspirate in a container, the container including a first filter element and a second filer element; and
    moving the first filter element relative to a second filter element within the container to separate cellular components of the lipoaspirate from non-cellular components of the lipoaspirate.

2. The method of claim 1 wherein the first filtering element has a pore size different from a pore size of the second filtering element.

3. The method of claim 1 wherein the first filtering element is capable of separating blood/tumescent fluids from cellular materials in lipoaspirate.

4. The method of claim 1 wherein the second filtering element is capable of separating oils from cellular materials in lipoaspirate.

5. The method of claim 1 further comprising observing the separation and stopping the moving when a desired degree of separation is achieved.

\* \* \* \* \*